(12) United States Patent
Regensburger et al.

(10) Patent No.: US 11,436,721 B2
(45) Date of Patent: Sep. 6, 2022

(54) MEDICAL IMAGING DEVICE, SYSTEM, AND METHOD FOR GENERATING A MOTION-COMPENSATED IMAGE, AND CORRESPONDING STORAGE MEDIUM

(71) Applicant: Siemens Healthcare GmbH, Erlangen (DE)

(72) Inventors: Alois Regensburger, Erlangen (DE); Jessica Magaraggia, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 421 days.

(21) Appl. No.: 16/733,943

(22) Filed: Jan. 3, 2020

(65) Prior Publication Data
US 2020/0219254 A1  Jul. 9, 2020

(30) Foreign Application Priority Data

Jan. 3, 2019 (EP) .................................. 19150243

(51) Int. Cl.
*G06K 9/00* (2022.01)
*G06T 7/00* (2017.01)
(Continued)

(52) U.S. Cl.
CPC ............ *G06T 7/0012* (2013.01); *A61B 34/20* (2016.02); *G06T 7/246* (2017.01); *G06T 7/60* (2013.01);
(Continued)

(58) Field of Classification Search
CPC ......... G06T 11/005; G06T 2207/30204; G06T 7/33
See application file for complete search history.

(56) References Cited

U.S. PATENT DOCUMENTS 8,204,172 B1 * 6/2012 Hsieh .................... G06T 11/006
378/4
9,826,942 B2 * 11/2017 Sebok ................... G06T 11/005
(Continued)

FOREIGN PATENT DOCUMENTS

DE    102013202313 A1    8/2014
JP    2012081202 A       4/2012
(Continued)

OTHER PUBLICATIONS

Japanese Office Action for Japanese Application No. 2019-190389 dispatched Aug. 10, 2021, with English translation.
(Continued)

*Primary Examiner* — Hadi Akhavannik
(74) *Attorney, Agent, or Firm* — Lempia Summerfield Katz LLC (57) ABSTRACT

A medical imaging device, a system, and a method for generating a motion-compensated image are provided. A corresponding method as well as a computer readable storage medium having stored thereon a corresponding computer program are also provided. Image data is captured and acquired while a deformable robotic instrument is in contact with a subject to be imaged. A data processor is configured to compensate for a motion of the subject by processing the image data in dependence on time-resolved motion and/or geometry data of the robotic instrument, and/or by generating a control signal for controlling the robotic instrument to counteract the motion of the subject.

17 Claims, 1 Drawing Sheet

(51) Int. Cl.
  *A61B 34/20* (2016.01)
  *G06T 7/246* (2017.01)
  *G06T 7/70* (2017.01)
  *G06T 7/60* (2017.01)

(52) U.S. Cl.
  CPC ........ *G06T 7/70* (2017.01); *A61B 2034/2046* (2016.02); *A61B 2562/00* (2013.01); *G06T 2207/10072* (2013.01); *G06T 2207/10121* (2013.01)

(56) References Cited

U.S. PATENT DOCUMENTS

| | | | |
|---|---|---|---|
| 9,867,549 B2* | 1/2018 | Ernst | A61B 5/7292 |
| 11,210,819 B2* | 12/2021 | Regensburger | A61B 6/5264 |
| 11,250,565 B2* | 2/2022 | Magaraggia | G06T 7/0012 |
| 11,282,211 B2* | 3/2022 | Regensburger | G06T 19/20 |
| 2005/0203373 A1* | 9/2005 | Boese | G06T 7/38 600/407 |
| 2009/0080737 A1 | 3/2009 | Battle | |
| 2011/0123081 A1* | 5/2011 | Sebok | G06T 7/33 382/131 |
| 2012/0116210 A1 | 5/2012 | Zino | |
| 2014/0226891 A1 | 8/2014 | Kunze | |
| 2015/0310586 A1 | 10/2015 | Florent | |
| 2016/0166205 A1* | 6/2016 | Ernst | A61B 5/1127 600/407 |
| 2016/0235383 A1 | 8/2016 | Bar-tal et al. | |
| 2016/0302757 A1* | 10/2016 | Pizaine | A61B 6/5241 |
| 2016/0364880 A1 | 12/2016 | Barratt et al. | |
| 2017/0007334 A1 | 1/2017 | Crawford | |
| 2017/0027419 A1 | 2/2017 | Belson et al. | |
| 2017/0238897 A1* | 8/2017 | Siewerdsen | A61B 6/466 |
| 2018/0368929 A1* | 12/2018 | Popovic | A61B 17/00234 |
| 2020/0093456 A1 | 3/2020 | Fischer et al. | |
| 2020/0250835 A1 | 8/2020 | Alzaga et al. | |

FOREIGN PATENT DOCUMENTS

| | | |
|---|---|---|
| JP | 2012096037 A | 5/2012 |
| JP | 2016503667 A | 2/2016 |
| JP | 2016147059 A | 8/2016 |
| JP | 2016537110 A | 12/2016 |
| JP | 2017080422 A | 5/2017 |
| JP | 2017512522 A | 5/2017 |

OTHER PUBLICATIONS

European Search Report cited in corresponding European Application No. 19150243.4-1124; dated Jul. 19, 2019.

Grangeat, Pierre et al., Theoretical framework for a dynamic cone-beam reconstruction algorithm based on a dynamic particle model, Physics in Medicine and Biology, vol. 47, pp. 2611-2626, 2002; 2002.

Hager G et al, Surgical and interventional robotics: part III, IEEE Robotics & Automation Magazine, IEEE Service Center, Piscataway, NJ, US, vol. 15, No. 4, Dec. 2, 2008, pp. 84-93; XP011355010, ISSN: 1070-9932, DOI: 10.1109/MRA.2008.930401; 2008.

Heimann, Tobias et al., Real-time ultrasound transducer localization in fluoroscopy images by transfer learning from synthetic training data, Medical Image Analysis, vol. 18, No. 8, pp. 1320-1328, 2014; 2014.

Rohkohl, C. et al., Interventional 4D motion estimation and reconstruction of cardiac vasculature without motion periodicity assumption, Medical Image Analysis, vol. 14, pp. 687-694, 2010; 2010.

S. Rit et al., On-the-fly motion-compensated cone-beam CT using an a priori model of the respiratory motion, Med. Phys., 2009, vol. 36, pp. 2283-2296, oi:10.1118/1.3115691.

Schäfer, Dirk et al., Motion-Compensated and Gated Cone Beam Filtered Back-Projection for 3-D Rotational X-Ray Angiography, IEEE Transactions on Medical Imaging, vol. 25, No. 7, pp. 898-906, Jul. 2006; 2006.

Sindel, Aline et al., Respiratory Motion Compensation for C-Arm CT Liver Imaging, Bildverarbeitung für die Medizin 2015; Springer Vieweg, Berlin, Heidelberg; DOI https://doi.org/10.1007/978-3-662-46224-9_39; Online ISBN 978-3-662-46224-9; 2015.

Syben, C.et al., Joint calibration and motion estimation in weight-bearing cone-beam CT of the knee joint using fiducial markers, 2017 IEEE 14th International Symposium on Biomedical Imaging (ISBI 2017), Melbourne, VIC, 2017, pp. 494-497. doi: 10.1109/ISBI.2017.7950568 http://ieeexplore.ieee.org/document/7950568/; 2017.

Japanese Office Action for Japanese Application No. 2019-190389 dispatched Mar. 9, 2021, with English translation.

* cited by examiner

FIG 1

FIG 2

MEDICAL IMAGING DEVICE, SYSTEM, AND METHOD FOR GENERATING A MOTION-COMPENSATED IMAGE, AND CORRESPONDING STORAGE MEDIUM This application claims the benefit of European Patent Application No. EP 19150243.4, filed on Jan. 3, 2019, which is hereby incorporated by reference in its entirety.

BACKGROUND

The present embodiments relate to generating a motion-compensated image of a subject.

Today, there are a number of different imaging techniques or imaging modalities for acquiring or generating anything from live two-dimensional (2D)-images to three-dimensional (3D)-images reconstructed from multiple 2D-projection images, 3D-computed tomography (CT)-datasets, and 3D-magnetic resonance imaging datasets. Even though these imaging techniques or modalities are by now established state of the art, efforts continue to improve an image quality of resulting images.

One problem negatively affecting image quality is a motion of an imaged subject during acquisition of respective image data. For example, the article "On-the-fly motion—compensated cone—beam CT using an a priori model of the respiratory motion" by Simon Rit et al., published in Medical Physics, 36: 2283-2296, doi: 10.1118/1.3115691 discusses the problem of a respiratory motion causing artifacts in cone-beam CT images acquired on slow rotating scanners. Therein, an a priori motion model of the patient respiratory cycle is estimated from a four-dimensional (4D) planning CT. During the acquisition, the model is correlated with the registration using a respiratory signal extracted from the cone beam projections. The estimated motion is then compensated for in an optimized reconstruction algorithm. The motion compensated for is forced to be null on average over the acquisition time to provide that the compensation results in a cone-beam CT image that describes the mean position of each organ, even if the a priori motion model is inaccurate.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved image quality is enabled in situations where an imaged subject is prone to movement during image data acquisition without a need for a priori estimates or a perfectly regular motion of the subject.

The present embodiments are relevant for medical imaging applications and medical images but may also be used or applied in other technical fields and applications.

A medical imaging device according to the present embodiments is adapted and configured for generating a motion-compensated image (e.g., a medical image) of a subject. The subject may, for example, be a patient or a part of a patient, such as an organ or a part of an organ. The medical imaging device includes a data acquisition device for acquiring image data of the subject, where the image data is or has been captured while a deformable robotic instrument is in contact with the subject and/or is arranged in a cavity of the subject or in proximity to the subject. The data acquisition device may include a medical imaging modality such as an x-ray device or a magnetic resonance imaging (MRI) device used for capturing the image data. In this case, capturing the image data be or include an actual detection or measurement of a signal encoding or carrying the image data by a detector, a sensor, or a measuring or receiving device. Acquiring the image data may then be or include taking or acquiring the captured image data (e.g., at a data interface), directing the image data to a data processing device and/or storing the image data on a data storage medium, so that the image data is available for processing.

The data acquisition device may, however, equally just include a data processing device equipped and configured for acquiring the captured image data (e.g., from a data storage medium or over a data interface).

The medical imaging device according to the present embodiments further includes a data processing system or a data processing device for compensating for the motion of the subject by processing the image data in dependence on motion and/or geometry data (e.g., time-resolved) of the robotic instrument. The motion and/or geometry data for the robotic instrument may include a pose of the robotic instrument, which may be tracked by a tracking system and provided to the, for example, data processing device by a tracking system, or which may be acquired from the tracking system by the data acquisition device. The motion of the subject during the acquisition of the image data may then be compensated since the motion is related to or given by the motion and/or geometry data of the robotic instrument due to the robotic instrument being in physical or mechanical contact or communication with the subject.

For example, the acquired image data may be or include a 3D-dataset or a 3D-scan of the subject, which may take a significant time to capture depending on the medical imaging device or imaging modality being used. During this time, the subject may move and significantly change position or pose, which may then also influence the motion and/or pose of the robotic instrument correspondingly or accordingly.

From the motion and/or geometry data of the robotic instrument, a motion or motion field of the subject or a part thereof may be determined. The motion of the subject may then be compensated for or corrected during or as part of reconstructing the motion-compensated image from the image data based on the motion field and therefore, at least indirectly, based on the motion and/or geometry data of the robotic instrument. The term "motion field" refers to a movement or motion of the parts or volume elements of the subject during the acquisition of the image data as spatially and time-resolved motion data. The motion of the subject during the acquisition may, for example, be or include a translatory and/or a rotational part and/or a deformation of the subject. The deformation of the subject or a part thereof may, for example, occur due to an interaction or contact between the subject and the robotic instrument.

The robotic instrument being deformable provides that the robotic instrument may change shape either actively or passively. For example, the robotic instrument may be flexible and/or articulated (e.g., having multiple joints). The robotic instrument may be actively deformable, providing that a form, shape, or geometry of the robotic instrument may be actively changed or controlled by one or more motors or actuators. It is, however, also possible for the robotic instrument to be passively deformable, providing that the robotic instrument may be deformed by the motion of the subject with which the robotic instrument is in physical or mechanical contact. This may allow for the motion of the subject or part thereof to be determined or measured in terms of a motion and/or the deformation of the robotic instrument and/or a force, momentum, or pressure acting upon the robotic instrument other than or independently of any force or momentum applied by the motor or actuator of the robotic instrument itself.

Additionally or alternatively, the data processing device, for example, is adapted and configured for compensating for the motion of the subject by generating a control signal for controlling the robotic instrument to counteract (e.g., minimize, hinder, or oppose) the motion of the subject. The motion of the subject is minimized or compensated for a respective next image or image data to be captured (e.g., a next projection image, frame, or image dataset). For example, it may be determined from the image data, an additional motion tracking system, and/or the motion and/or geometry data of the robotic instrument, that the subject is moving relative to the robotic instrument and/or deforming or pushing on the robotic instrument. The robotic instrument may then be controlled or moved in an opposite direction of the motion of the subject, so that the subject essentially stays stationary with respect to a coordinate system of the medical imaging device or the imaging device or modality used for capturing the image data.

It is also possible to stiffen the robot to resist any deformation and/or motion or pressure exerted by the subject on the robotic instrument. The robotic instrument may then function as a brace for the subject (e.g., to stop or prevent a collapse of a lung, or the like). If, for example, the robot is stiffened so that the robot may no longer be deformed by the subject, the robotic instrument may then still be moved and deform or push the subject. This may counteract a natural motion of the subject to keep the subject essentially stationary. This may also cause a motion of the subject, which may then, however, be compensated for in a resulting or reconstructed image since the motion of the subject is known from or given by the motion of the robotic instrument and may therefore be taken into account in generating the image.

The data processing system or data processing device may, for example, be or include a computer with a data store and a processor connected thereto. A computer program or operating system for the data processing device, for example, and/or for the medical imaging device may be stored on the data store. The computer program or operating system, when executed by the processor, causes the data processing device, for example, or the medical imaging device to carry out the acts or actions described herein.

Using the robotic instrument as a basis for correcting or compensating the motion of the subject (e.g., also for sensing, detecting, or determining the motion of the subject) has the advantage that the motion-compensated image may be generated with improved image quality. For example, this may be achieved without or with a reduced need for additional tracking markers, additional applications of a contrast agent to the subject, and/or continuous high dosage imaging of the subject. For example, using the present embodiments, a motion-compensated image may be generated for a lung of a patient during a bronchoscopy even though there typically is no highly contrasted vessel tree available as a reference. This provides that the present embodiments may provide improved image quality in more or different situations and/or with reduced exposure or stress for the subject when compared to traditional methods. Also, slower 3D-imaging devices may be used to acquire a 3D-image or a 3D-scan of a subject without the image or scan being unusable due to motion artifacts or blurring. In effect, the present embodiments provide an advantageous synergy between a robotic instrument and a medical imaging device.

In summary, the motion and/or geometry data and/or the controllability of the robotic instrument may be used as a basis for generating a motion-compensated image through a corresponding computation during image reconstruction and/or through preventing or minimizing motion of the subject during image data acquisition.

The motion and/or geometry data may, for example, be acquired from corresponding tracking data of a tracking system used for tracking the robotic instrument. The tracking system may, for example, be or include an electromagnetic tracking system or device. Other possibilities are described below.

A possible workflow for realizing the advantages of the present embodiments may include: acquiring the image data; determining the pose or a change in pose of the robotic instrument; from that, calculating a motion field of the subject or a part of the subject in proximity or in contact with the robotic instrument; and then, correcting or compensating for this motion for the motion-compensated image that is to be generated based on the acquired image data and the motion field. Reconstructing, for example, a motion-compensated 3D-image of a subject from a 3D-scan or 3D-dataset using a motion field of the imaged subject may automatically be performed relatively straightforwardly using established standard methods. The present embodiments do, however, provide a useful way of acquiring this motion field.

In an embodiment, the medical imaging device is configured to acquire the motion and/or geometry data according to a positional sensor system of the robotic instrument from a control unit controlling the robotic instrument. In other words, the robotic instrument, or a robotic system of which the robotic instrument is a part, provides the motion and/or geometry data itself. This provides that an external tracking system that advantageously reduces a complexity and effort needed for using and applying the present embodiments is not needed. Also, this way, the present embodiments may function particularly reliably since, for example, issues of obfuscation or interference of or with an external tracking system may be avoided.

Additionally, the sensor system of the robotic instrument may also provide force and/or momentum data indicating a force, momentum, and/or pressure applied to the robotic instrument. These quantities may not easily be measured using an external tracking system but may allow for an improved modelling, simulation, or estimation of the motion (e.g., a deformation) of the subject. The sensor system of the robotic instrument may, for example, include one or more accelerometers, fibre Bragg gratings, inertial measurement units (IMUs), strain sensors, force sensors, pressure sensors, angulation sensors, and/or the like for one or multiple parts, segments, actuators, joints, and/or axis of the robotic instrument.

The sensor system of the robotic instrument, a positioning or navigation system of the robotic instrument including the sensor system, or processing sensor data provided by the sensor system may also include an internal model of the robotic instrument itself to determine and keep track of the motion and/or geometry data (e.g., the pose) of the robotic instrument. For example, joint positions or angulations of joints of the robotic instrument may be automatically measured and/or determined and tracked based on the motion and/or geometry data according to the positional sensor system.

The motion and/or geometry of the robotic instrument may be measured or determined relative to an initial or starting pose or reference pose of the robotic instrument. The motion and/or geometry of the robotic instrument may also be determined or tracked with respect to an internal coordinate system of the robotic instrument, a coordinate system, fixed with respect to the world or a surrounding room, and/or a coordinate system of the medical imaging device and/or the imaging modality used to capture the image data. If more than one of these coordinate systems is used in applying the present embodiments, an automatic or semiautomatic registration between these coordinate systems may be performed to allow a consistent processing and combination of the motion and/or geometry data of the robotic instrument and the captured and acquired image data.

In a further advantageous development of the present embodiments, the medical imaging device is configured to determine the motion and/or geometry data of the robotic instrument at least in part from the acquired image data (e.g., by automatically detecting an outline of the robotic instrument and/or a pose of at least one positional marker attached to the robotic instrument in the image data). This provides that and an image-based approach may be taken to acquire the necessary motion and/or geometry data of the robotic instrument needed for performing the motion compensation correction for the resulting final image of the subject. This approach may be particularly useful and easy to implement since the image data is captured anyway so that no additional hardware or preparation is required and the robotic instrument may relatively easily be built and/or the imaging device or modality may be adapted or tuned so that the robotic instrument may reliably be detected in the image data. For example, the robotic instrument may contain metal parts that are more easily detectable and discernible than, for example, a soft tissue of the subject under x-ray imaging. This provides that the robotic instrument may be reliably identified and tracked through the image data essentially independently of in which part of a patient the robotic instrument is located. This image-based tracking of the robotic instrument may be combined with any or all of the other possibilities for acquiring the motion and/or geometry data described herein. This may result in an overall improved accuracy and/or reliability of the motion and/or geometry data and therefore in a further improved image quality.

In a further development of the present embodiments, the data processing device contains a predetermined biomechanical model of at least part of the subject and is configured to provide the motion and/or geometry data of the robotic instrument and/or changes thereof over time as input to the biomechanical model. The data processing device is further configured to generate the motion-compensated image based on the image data and a behavior of the subject according to the biomechanical model. The biomechanical model may model, simulate, or characterize a mechanical behavior of the subject, an elasticity of the subject, fluid dynamic properties of the subject, compressibility of the subject, limits to possible motions and/or possible deformations of the subject due to internal structure, surrounding tissues, and/or connections thereto, and/or the like. Such a biomechanical model may be prepared in advance with essentially arbitrary accuracy. Adapting or tuning the biomechanical model may allow for real-time modelling or simulating and consequently, compensating the motion of the subject, for example, by limiting a number of parameters and/or a resolution, as well as maximum accuracy for the best achievable image quality in situations where real-time imaging is not essential.

In a simple case, an average motion or the deformation of the robotic instrument may be determined and applied to the subject. This provides that the subject or part of the subject in a predetermined region of interest may be treated or regarded as an essentially rigid object that moves according to (e.g., in the same manner or way) as the robotic instrument. This may significantly reduce a computational complexity and therefore allow for motion compensation even with relatively low performance computational hardware. In a more advanced application, the motion of the robotic instrument and/or a change in the geometry or shape of the robotic instrument over time (e.g., in a predetermined part or region of interest) may be extrapolated to the biomechanical model of the subject (e.g., a model of a complete organ).

For example, the robotic instrument may move and/or change geometry due to a respiratory motion. The robotic instrument may, for example, form or follow a curved line. A curvature of the curved line may periodically change due to the respiratory motion of a lung, in which the robotic instrument is arranged. Rather than assuming a merely translatory motion of the subject (e.g., the lung) according to the motion or change in geometry of the robotic instrument, an expansion and contraction of the lung may be modelled according to the measured or detected motion and/or change in geometry of the robotic instrument by driving the biomechanical model of the subject with the motion and/or geometry data as input. This may provide a more accurate modelling or simulation of the motion of the subject.

The actual motion and/or geometry data of the robotic subject may be used as a reference for the actual motion of the subject, providing that no assumptions about a periodicity or regularity of the motion of the subject have to be made. Using the actually measured motion and/or geometry data of the robotic instrument may also provide a more accurate and reliable basis for the motion compensation than, for example, an extrapolation of the motion of the subject from a preoperative measurement of, for example, the respiratory movements of the subject.

In a development, the motion and/or geometry data of the robotic instrument provides multiple supporting points for the biomechanical model (e.g., for the motion of the subject). This provides that the motion and/or geometry of the robotic instrument is determined and tracked at multiple points of the robotic instrument along a length. This may allow for accurately modelling the motion of the subject along curved sections or outlines (e.g., organ boundaries). The biomechanical model of the subject may, for example, be generated automatically, semi-automatically, or manually based on a preoperative CT-scan and/or MRI-scan. Alternatively, the biomechanical model is based on an image reconstructed from the image data. Therein, other approaches for motion compensation known from the state of the art may or may not be used.

In a further development of the present embodiments, the data processing device, for example, contains a predetermined stiffness value of or for the robotic instrument (e.g., relative to a predetermined stiffness of at least part of the subject) and is configured to automatically estimate a deformation of at least part of the subject based on the motion and/or geometry data of the robotic instrument with the stiffness value as a parameter. Depending on the stiffness of the robotic instrument (e.g., relative to the stiffness of surrounding parts of the subject), a particular deformation and/or motion of the robotic instrument may translate to or be caused by or correspond to different amounts of motion and/or the formation of the subject. Taking into account the stiffness of the robotic instrument and, for example, the stiffness of the subject thus enables a more accurate modelling, simulation, or determination of the actual motion and/or deformation of the subject, and therefore a further improved quality and accuracy of the motion-compensated image. For example, the stiffness of the robotic instrument may be provided spatially resolved for different parts of the robotic instrument, and may be automatically and dynamically updated according to, for example, a control scheme and/or a shape and/or joint positions of the robotic instrument. For example, the effective stiffness of the robotic instrument may depend on a current actuation and/or geometry of the robotic instrument. Thus, providing the stiffness value of the robotic instrument as spatially and temporally resolved data may further improve the accuracy of the determined motion of the subject, and therefore the image quality and accuracy of the motion-compensated image.

In a further development of the present embodiments, the data processing device, for example, is configured to automatically determine and take into account for compensating the motion of the subject a region of space in which the robotic instrument may move freely without getting in direct physical contact with the subject. It is, in other words, determined if the robotic instrument or part thereof is arranged in a cavity or outside of the subject and may therefore be moved and/or deformed without interacting with the subject (e.g., without causing the subject to move or deform). This provides that any motion data and/or geometry data of the robotic instrument is not necessarily directly translated into a corresponding motion of the subject. The region of space or the cavity may, for example, be automatically or semi-automatically determined from the image data through segmentation.

It may also be possible to predetermine when and/or where the robotic instrument may move without contacting the subject based on a preoperative planning based on a preoperative 3D-image of the subject. Recognizing and taking into account this possibility for the motion and/or geometry of the robotic instrument to not always directly correspond to a motion of the subject may further improve the image quality of the motion-compensated image of the subject.

It is also possible to determine whether the robotic instrument is moving freely or in contact with the subject based on sensor data of the robotic instrument (e.g., one or more pressure or force sensors of the robotic instrument). If the robotic instrument is moving without a pressure sensor, which may, for example, be arranged on a surface of the robotic instrument, registering any increased or changing pressure as compared to a reference pressure of the robotic instrument in air, it may be determined that at least the pressure sensor or a corresponding part of the robotic instrument where the pressure sensor is arranged or mounted is currently not in direct physical contact with the subject. In other words, the motion of the subject may be compensated in dependence on sensor data of the robotic instrument (e.g., pressure and/or force sensor data), indicating whether or not the robotic instrument is in mechanical contact with the subject.

In a further development of the present embodiments, the data processing device, for example, is configured to prioritize compensating the motion of the subject in a predetermined region of interest of the subject. The motion is, in other words, compensated for or in the region of interest, while other parts of the image are allowed to have more or stronger blurring or motion artifacts if these cannot be avoided or compensated over the entire image. This may result in improved diagnostic possibilities and/or an interventional success when compared to traditional methods, where the motion compensation might be averaged over the entire image. The predetermined region of interest may, for example, be automatically determined as a given region or area around a detected lesion or anatomical abnormality, and/or may be marked by a physician or technician.

In a further development of the present embodiments, the data processing device, for example, is configured to prioritize motion and/or geometry data for a tip of the robotic instrument over motion and/or geometry data for a rest of the robotic instrument. This provides that the motion and position or pose of the tip of the robotic instrument may be assigned a stronger or larger weight in a motion compensation calculation. This results in the motion being most effectively or most accurately compensated or corrected in or for a respective area or region where the tip of the robotic instrument is currently located. In one embodiment, an image of a tissue closely or directly surrounding the tip of the robotic instrument may then be reconstructed with a particularly high image quality. This may allow a user to more accurately or precisely and reliably navigate the tip of the robotic instrument and may therefore improve a result of an intervention and/or make achieving a successful outcome easier. This development of the present embodiments takes into account that, because of the deformability or flexibility of the robotic instrument, different motions of different parts or segments of the robotic instrument may lead to conflicting data for a simplified model of the subject and resolves these conflicts. Since the tip of the robotic instrument is typically where an interaction between the robotic instrument and the subject occurs, prioritizing the motion of the tip of the robotic instrument is advantageous.

In a further development of the present embodiments, the data processing device, for example, is configured to generate the motion-compensated image from at least one fluoroscopy image that is or has been captured as the image data of the subject, and from an overlay image overlaid on the fluoroscopy image. The data processing device is then further configured to automatically adapt a position of the overlay image relative to the fluoroscopy image based on the motion and/or geometry data of the robotic instrument. The fluoroscopy image and the overlay image may, for example, be overlaid on top of each other using a known 2D/3D-overlay or superimposition technique. The overlay image may, for example, be or include preoperative image data, such as an original image and position of at least part of the subject, planning data, such as an instrument path, a virtual model of parts of the subject, and/or of the robotic instrument, and/or the like. Based on the motion and/or geometry data (e.g., time-resolved) of the robotic instrument, the motion compensation may then be performed to keep the overlay image correctly aligned with the live fluoroscopy image even during movement or motion of the subject, and/or the robotic instrument. Since the overlay image may be prepared in advance while the fluoroscopy image is a live image, a motion of the subject relative to a position of the subject at a time when the overlay image was prepared would otherwise lead to a misalignment between the overlay image and the fluoroscopy image. Since the actual motion of the subject during capturing of the fluoroscopy image may be determined based on the motion and/or geometry data of the robotic instrument, the motion of the subject does not necessarily need to be determined based on the image data (e.g., the fluoroscopy image itself). This provides that the motion compensation may be achieved with a reduced amount of contrast agent and/or a reduced frame rate for the acquisition or capturing of the fluoroscopy image, thereby enabling reduced strain or reduced detrimental impact on the subject.

Another aspect of the present embodiments is a system including the medical imaging device according to the present embodiments as well as the mentioned robotic instrument, where the robotic instrument and/or a control unit controlling the robotic instrument is configured to interface with the medical imaging device for transmitting the motion and/or geometry data of the robotic instrument to the medical imaging device. The robotic instrument of the system according to the present embodiments may, in other words, be the robotic instrument mentioned in conjunction with the medical imaging device according to the present embodiments. The system according to the present embodiments may therefore have or include any or all of the properties and/or components or parts mentioned in conjunction with the medical imaging device according to the present embodiments.

Another aspect of the present embodiments is a method for motion compensation for images (e.g., for medical images) of a subject. The method includes acquiring image data of the subject, where the image data is or has been captured while a deformable robotic instrument is in contact with the subject, and/or arranged in a cavity of the subject or in proximity to the subject. The method according to the present embodiments further includes generating a motion-compensated image of the subject by processing the image data in dependence on motion and/or geometry data of the robotic instrument, and/or by controlling the robotic instrument to counteract a motion of the subject. The method according to the present embodiments may also include, as further, possibly optional, process acts any acts or actions described in conjunction with the other aspects of the present embodiments (e.g., in conjunction with the medical imaging device and/or the system according to the present embodiments).

The medical imaging device and/or the system according to the present embodiments may be configured to automatically or semi-automatically carry out the method according to the present embodiments. For example, for this purpose, the method according to the present embodiments or respective process acts may be computer-implemented. This provides that the method according to the present embodiments may take the form of a computer program or program code, including instructions that when carried out by the medical imaging device and/or the system according to the present embodiments cause these to perform or carry out the method according to the present embodiments. Such a computer program or program code is in itself another aspect of the present embodiments.

Another aspect of the present embodiments is a computer readable storage medium (e.g., a non-transitory computer-readable storage medium) having stored thereon a computer program that includes instructions that, when executed by a computer (e.g., by the data processing device) or device of the medical imaging device and/or the system according to the present embodiments, cause the computer to carry out the method according to the present embodiments.

The medical imaging device and/or the system according to the present embodiments may include a computer-readable storage medium according to the present embodiments as well as a respective process or processing device, such as a microchip, microprocessor, or microcontroller, for carrying out the computer program or program code stored on the respective computer-readable storage medium.

The present embodiments may be used, applied, or executed during or in parallel to an interventional procedure. Any corresponding surgical acts or procedures may not be part of the present embodiments.

The embodiments and developments described herein for at least one aspect (e.g., at least for the medical imaging device, the system, the method, the computer program, and the computer-readable storage medium), as well as the corresponding advantages, may be applied to any and all aspects of the present embodiments.

Further advantages, features, and details of the present embodiments derive from the following description of exemplary embodiments as well as from the drawings pertaining to the present embodiments. The features and feature combinations previously mentioned in the description, as well as the features and feature combinations mentioned in the following description of the figures and/or shown in the figures alone may be employed not only in the respectively indicated combination but also in other combinations, or taken alone without leaving the scope of the present embodiments.

DETAILED DESCRIPTION

The examples described below refer to exemplary embodiments. Therein, individual components and process acts of the embodiments each constitute individual, independent features of the present embodiments that may further develop the invention independently of each other as well as in combinations not explicitly described. The described embodiments may be further developed or supplemented by features, components, and/or acts already described above.

Figure 1:
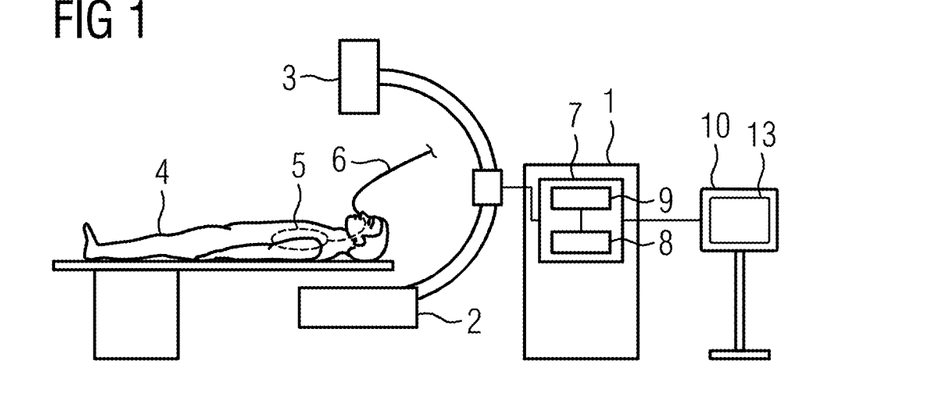
FIG. 1 is a schematic drawing of one embodiment of a medical imaging device configured to generate a motion-compensated image of a subject.

FIG. 1 schematically shows one embodiment of a medical imaging device 1 for capturing and acquiring image data of a subject. The imaging device 1 includes a rotatable C-arm on which a radiation source 2 and a corresponding detector 3 are mounted. A patient 4 is arranged between the radiation source 2 and the detector 3, with a lung 5 of the patient 4 as the subject to be imaged. The C-arm of the imaging device 1 is configured for capturing a three-dimensional (3D)-dataset or 3D-scan of the lung 5. This may, however, take a significant amount of time, which is not negligible in comparison to a speed of movement or motion of the patient 4 or parts of the patient 4, such as the lung 5, for example, during regular breathing. Depending on a concrete model of the imaging device 1, which may, for example, be any one of multiple different types or models of x-ray device, computed tomography device, magnetic resonance imaging (MRI) device, and/or the like, capturing the complete 3D-dataset may, for example, take up to 30 seconds. In many cases, the patient 4 may only be lightly sedated and/or may not be given artificial respiration, which makes control over the respiratory motion difficult or impossible. Even in cases where the patient 4 holds his breath during acquisition of the image data, a motion or movement of the patient 4 or parts thereof (e.g., of the lung 5) may still occur (e.g., due to a heartbeat of the patient 4).

The lung 5 may be the subject for an examination or intervention during a bronchoscopy. A contrasted vessel tree is typically not available as a basis for an image-based motion compensation like may be possible for images of a liver or a brain of the patient 4. In general, blurring or motion artifacts for anatomical structures of the patient 4 may occur in the captured image data due to motion or movement of the patient 4 or parts thereof (e.g., for images of an abdomen or thorax of the patient 4). This may hinder or impede a reliable and accurate diagnosis as well as navigation of medical instruments and/or treatment. To enable reliable and accurate diagnoses and support for treatments or interventions, two-dimensional (2D)- or 3D-images of the patient 4 during an examination or intervention with improved image quality (e.g., in terms of reduced blurring and motion artifacts) would be desirable.

For example, during an examination or intervention where a medical instrument is already applied to or inserted into the patient 4, a 3D-image of the patient 4 may be captured or acquired relatively slowly as image data to picture a current anatomical situation, including any displacements or deformation of parts of the patient 4, caused by a medical instrument in three dimensions.

A situation is pictured where a deformable, flexible robotic instrument 6 is partly arranged or guided into the lung 5 of the patient 4. Prior to this situation pictured in FIG. 1, a pre-op 3D-dataset of the patient 4 (e.g., the lung 5) may have been acquired for detecting and marking any regions of interest and planning the intervention or procedure. From this pre-op 3D-dataset, a biomechanical model of the lung 5 may be generated.

For processing any such image data and any additional data, such as a virtual model, an planned path, and/or the like, the imaging device 1 also includes a data processing unit or data processing device 7 that includes a computer-readable data store 8, as well as a processor 9 connected thereto. The data processing device 7 is presently configured to process any available data to generate a motion-compensated image 13 (see also FIG. 2) of the respective subject, which in this case, is the lung 5. The motion-compensated image 13 may then be displayed on a display device 10 that may be part of the imaging device 1 or connected thereto.

Figure 2:
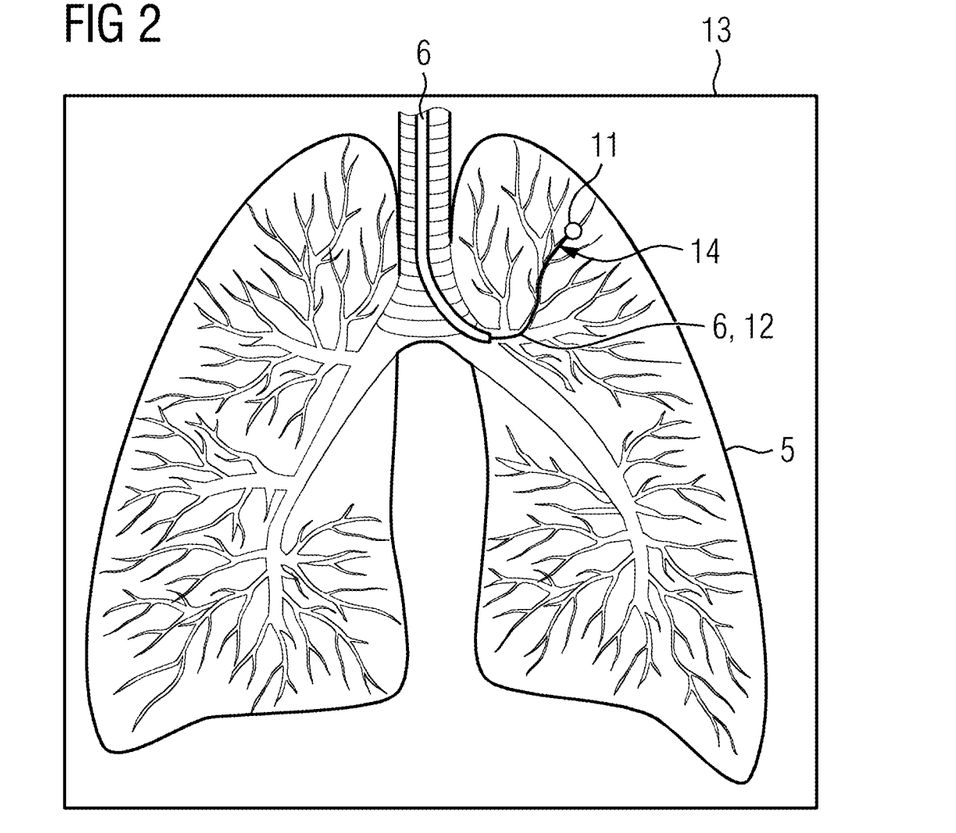
FIG. 2 is a schematic drawing of a subject and one embodiment of a flexible robotic instrument.

FIG. 2 schematically shows an example of the motion-compensated image 13, which shows the lung 5 with the robotic instrument 6 partly inserted. A lesion 11 of the lung 5 has been identified as a region of interest, and a corresponding planned instrument path 12 is indicated as an overlay image. The robotic instrument 6 is shown in FIG. 2 following the instrument path 12 with an instrument tip 14 almost having reached the lesion 11. While navigating the robotic instrument 6 along the instrument paths 12, deformation of the robotic instrument 6 and/or the lung 5 may occur due to contact between the two.

To accurately perform the motion compensation to generate the motion-compensated image 13, a motion field of the lung 5, which describes the motion of the lung 5 during capturing of the image data for the 3D-image during the examination or intervention, is sought.

Time-resolved motion and/or geometry data of an internal positional sensor system of the robotic instrument 6 is to be converted into the motion field of the lung 5. Based on this motion field, a motion-compensated reconstruction of the 3D-image is then performed to prevent or suppress motion artifacts. This method works because a motion of the lung 5 also acts upon the robotic instrument 6 due to physical or mechanical contact and may then be detected by the sensor system of the robotic instrument 6. Also, if the robotic instrument 6 is being actively moved or controlled or actuated while in mechanical contact with the lung 5, the motion or geometry change of the robotic instrument 6 may be transferred to or imparted on the lung 5. In this case, the actual motion or geometry change of the robotic instrument 6 is known from the internal sensor system of the robotic instrument 6 and/or given by corresponding controlling commands or instructions issued to one or more motors or actuators of the robotic instrument 6.

The robotic instrument 6 may, for example, be a flexible robotically controllable catheter or endoscope (e.g., in the form of a "snake robot"). In one embodiment, the robotic instrument 6 is at least partly visible in the image data (e.g., x-ray visible). For this purpose, the robotic instrument 6 may include one or more x-ray visible markers or fiducials enabling an image-based detection and tracking of the robotic instrument 6 and corresponding motion and/or geometry, or a change thereof. The robotic instrument 6, a control unit of the robotic instrument 6, and/or the data processing device 7 may contain a model of the robotic instrument 6 as a basis for controlling and navigating the robotic instrument 6 and determining a pose of the robotic instrument 6. This model may be or include a discrete or continuous distortion model or bending model for the robotic instrument 6. A coordinate system of the robotic instrument 6 or a control unit of the robotic instrument 6 (e.g., an internal positional sensor system) may be registered to a coordinate system of the imaging device 1 using any of a number of established and well-known registration methods.

Additionally, the data processing device 7 may be configured to take into account additional parameters, boundary conditions, and/or data, as has been described above.

For example, the motion compensation may be prioritized for a region around the instrument tip 14 that, for example, includes the lesion 11.

The described examples show how sensor data of a flexible robot or instrument may be used for motion compensation (e.g., for CT-images and/or overlays) to enable an improved image quality.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging device for generating a motion-compensated image of a subject, the medical imaging device comprising:
   a data acquisition device configured to acquire image data of the subject, wherein the image data is captured while a deformable robotic instrument is in contact with the subject, is arranged in a cavity of the subject, or is in contact with the subject and is arranged in the cavity of the subject; and
   a data processor configured to compensate for a motion of the subject, the compensation for the motion of the subject comprising:

processing of the image data in dependence on motion of the robotic instrument, geometry data of the robotic instrument, or the motion and the geometry data of the robotic instrument;
generation of a control signal for controlling the robotic instrument to counteract the motion of the subject; or
a combination thereof.

2. The medical imaging device of claim 1, wherein the medical imaging device is configured to acquire the motion, the geometry data, or the motion and the geometry data according to a positional sensor system of the robotic instrument from a control unit controlling the robotic instrument.

3. The medical imaging device of claim 1, wherein the medical imaging device is configured to determine the motion, the geometry data, or the motion and the geometry data of the robotic instrument at least in part from the acquired image data.

4. The medical imaging device of claim 3, wherein the determination of the motion, the geometry data, or the motion and the geometry data of the robotic instrument comprises automatic detection of an outline of the robotic instrument, a pose of at least one positional marker attached to the robotic instrument, or the outline of the robotic instrument and the pose of the at least one positional marker in the image data.

5. The medical imaging device of claim 1, wherein the data processor contains a predetermined biomechanical model of at least part of the subject and is further configured to:
provide the motion, the geometry data, or the motion and the geometry data of the robotic instrument, changes thereof, or a combination thereof over time as input to the biomechanical model; and
generate the motion-compensated image based on the image data and a behavior of the subject according to the biomechanical model.

6. The medical imaging device of claim 1, wherein the data processor contains a predetermined stiffness value for the robotic instrument and is further configured to estimate a deformation of at least part of the subject based on the motion, the geometry data, or the motion and the geometry data of the robotic instrument with the stiffness value as a parameter.

7. The medical imaging device of claim 1, wherein the data processor is further configured to determine and take into account for compensating the motion of the subject a region of space in which the robotic instrument is movable without getting in direct physical contact with the subject.

8. The medical imaging device of claim 1, wherein the data processor is further configured to prioritize compensating the motion of the subject in a predetermined region of interest of the subject.

9. The medical imaging device of claim 1, wherein the data processor is further configured to prioritize motion, geometry data, or the motion and the geometry data for a tip of the robotic instrument over motion, geometry data, or the motion and the geometry data for a rest of the robotic instrument.

10. The medical imaging device of claim 1, wherein the data processor is further configured to:
generate the motion-compensated image from at least a fluoroscopy image that has been captured as the image data of the subject and an overlay image overlaid on the fluoroscopy image; and
automatically adapt a position of the overlay image relative to the fluoroscopy image based on the motion, the geometry data, or the motion and the geometry data of the robotic instrument.

11. A system comprising:
a medical imaging device for generating a motion-compensated image of a subject, the medical imaging device comprising:
a data acquisition device configured to acquire image data of the subject, wherein the image data is captured while a deformable robotic instrument is in contact with the subject, is arranged in a cavity of the subject, or is in contact with the subject and is arranged in the cavity of the subject; and
a data processor configured to compensate for a motion of the subject, the compensation for the motion of the subject comprising:
processing of the image data in dependence on motion of the robotic instrument, geometry data of the robotic instrument, or the motion and the geometry data of the robotic instrument;
generation of a control signal for controlling the robotic instrument to counteract the motion of the subject; or
a combination thereof; and
the robotic instrument,
wherein the robotic instrument, a controller of the robotic instrument, or the robotic instrument and the controller of the robotic instrument are configured to interface with the medical imaging device for transmitting the motion, the geometry data, or the motion and the geometry data of the robotic instrument to the medical imaging device.

12. A method for motion compensation for images, the method comprising:
acquiring image data of a subject, wherein the image data has been captured while a robotic instrument is in contact with the subject, is arranged in a cavity of the subject, or is in contact with the subject and is arranged in the cavity of the subject, the robotic instrument being deformable; and
generating a motion-compensated image of the subject, the generating of the motion-compensated image of the subject comprising processing the image data in dependence on motion of the robotic instrument, geometry data of the robotic instrument, or the motion and the geometry data of the robotic instrument, controlling the robotic instrument to counteract a motion of the subject, or a combination thereof.

13. The method of claim 12, further comprising acquiring the motion, the geometry data, or the motion and the geometry data according to a positional sensor system of the robotic instrument from a control unit controlling the robotic instrument.

14. The method of claim 12, further comprising determining, by a medical imaging device, the motion, the geometry data, or the motion and the geometry data of the robotic instrument at least in part from the acquired image data.

15. In a non-transitory computer-readable storage medium that stores instructions executable by a computer for motion compensation for images, the instructions comprising:
acquiring image data of a subject, wherein the image data has been captured while a deformable robotic instrument is in contact with the subject, is arranged in a cavity of the subject, or is in contact with the subject and is arranged in the cavity of the subject; and generating a motion-compensated image of the subject, the generating of the motion-compensated image of the subject comprising processing the image data in dependence on motion of the robotic instrument, geometry data of the robotic instrument, or the motion and the geometry data of the robotic instrument, controlling the robotic instrument to counteract a motion of the subject, or a combination thereof.

16. The non-transitory computer-readable storage medium of claim 15, wherein the instructions further comprise acquiring the motion, the geometry data, or the motion and the geometry data according to a positional sensor system of the robotic instrument from a control unit controlling the robotic instrument.

17. The non-transitory computer-readable storage medium of claim 15, wherein the instructions further comprise determining, by a medical imaging device, the motion, the geometry data, or the motion and the geometry data of the robotic instrument at least in part from the acquired image data.

\* \* \* \* \*